United States Patent
Singh

(10) Patent No.: US 9,739,689 B2
(45) Date of Patent: Aug. 22, 2017

(54) TIRE CORNERING STIFFNESS ESTIMATION SYSTEM AND METHOD

(71) Applicant: The Goodyear Tire & Rubber Company, Akron, OH (US)

(72) Inventor: Kanwar Bharat Singh, Stow, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 320 days.

(21) Appl. No.: 14/549,845

(22) Filed: Nov. 21, 2014

(65) Prior Publication Data

US 2016/0146706 A1 May 26, 2016

(51) Int. Cl.
| G01M 17/02 | (2006.01) |
| G01N 3/56 | (2006.01) |
| B60C 99/00 | (2006.01) |
| B60T 8/00 | (2006.01) |
| B60T 8/172 | (2006.01) |

(52) U.S. Cl.
CPC ............. *G01M 17/02* (2013.01); *B60C 99/00* (2013.01); *B60T 8/00* (2013.01); *B60T 8/1725* (2013.01); *G01N 3/56* (2013.01)

(58) Field of Classification Search
CPC ......... B60C 99/00; B60T 8/00; B60T 8/1725; G01M 17/02; G01N 3/56
USPC ...................................... 73/8, 146
See application file for complete search history.

(56) References Cited

U.S. PATENT DOCUMENTS

| 5,553,491 | A | * | 9/1996 | Naito .................... B60C 23/062 73/146.5 |
| 5,817,935 | A | * | 10/1998 | Di Bernardo ....... G01M 17/022 73/146 |
| 6,637,276 | B2 | | 10/2003 | Adderton et al. |
| 6,697,726 | B2 | | 2/2004 | Takagi et al. |
| 6,962,075 | B2 | | 11/2005 | Bertrand |
| 7,130,735 | B2 | | 10/2006 | Brown et al. |
| 7,404,317 | B2 | | 7/2008 | Mancosu et al. |

(Continued)

FOREIGN PATENT DOCUMENTS

| DE | 10320828 | 12/2004 |
| EP | 2301769 A1 | 3/2011 |

(Continued)

OTHER PUBLICATIONS

Der Einfluss der Fahrbahnoberflachenkrummung auf den Rollwiderstand, die Cornering Stiffness and die Aligning Stiffness von Pkw-Reifen by Unrau, KIT Scientific Publishing, Published Jul. 4, 2013.

(Continued)

*Primary Examiner* — Daniel S Larkin
(74) *Attorney, Agent, or Firm* — Edward T. Kennedy

(57) ABSTRACT

A tire cornering stiffness estimation system and method includes multiple tire-affixed sensors mounted to a supportive vehicle tire for operably measuring tire-specific parameters and generating tire-specific information relating tire pressure, temperature, wear state, tire identification and tire loading. One or more accelerometer(s) are mounted to the hub supporting the tire to generate a hub accelerometer signal. A model-based tire cornering stiffness estimator is included to generate a model-derived tire cornering stiffness estimation based upon the hub accelerometer signal adapted by the tire-specific information.

8 Claims, 17 Drawing Sheets

(56) References Cited

U.S. PATENT DOCUMENTS

| | | |
|---|---|---|
| 7,546,764 B2 | 6/2009 | Morinaga |
| 7,552,628 B2 | 6/2009 | Mancosu |
| 2002/0059023 A1 | 5/2002 | Takagi et al. |
| 2003/0236603 A1 | 12/2003 | Lu |
| 2004/0199314 A1 | 10/2004 | Meyers et al. |
| 2004/0254707 A1 | 12/2004 | Lu et al. |
| 2005/0033486 A1 | 2/2005 | Schmitt et al. |
| 2005/0072223 A1 | 4/2005 | Fennel et al. |
| 2005/0085987 A1 | 4/2005 | Yokota et al. |
| 2005/0150283 A1 | 7/2005 | Shick |
| 2005/0177296 A1 | 8/2005 | Brown et al. |
| 2007/0010928 A1 | 1/2007 | Brusarosco et al. |
| 2007/0017727 A1 | 1/2007 | Messih et al. |
| 2008/0103659 A1 | 5/2008 | Mancosu |
| 2009/0055040 A1 | 2/2009 | Nagaya |
| 2010/0063671 A1 | 3/2010 | Fink et al. |
| 2011/0060500 A1 | 3/2011 | Irth et al. |
| 2011/0199201 A1 | 8/2011 | Brusarosco et al. |
| 2013/0013143 A1* | 1/2013 | Wang .................... G01M 17/06 701/31.6 |
| 2013/0151075 A1 | 6/2013 | Moshchuk et al. |
| 2013/0211621 A1 | 8/2013 | Breuer et al. |
| 2014/0100754 A1* | 4/2014 | Schwindt .............. B60K 31/00 701/93 |

FOREIGN PATENT DOCUMENTS

| | | |
|---|---|---|
| EP | 2172760 A4 | 8/2012 |
| EP | 2777956 A2 | 9/2014 |
| EP | 1457388 B1 | 1/2015 |
| WO | WO2011054363 A1 | 5/2011 |

OTHER PUBLICATIONS

EPO search report received by Applicant on Jun. 27, 2016.

* cited by examiner

| 33 psi | | 37 psi | | 41 psi | | 45 psi | |
|---|---|---|---|---|---|---|---|
| p00= | −23.23 | p00= | 126.6 | p00= | 98.89 | p00= | −107.9 |
| p10= | −179.5 | p10= | −178.9 | p10= | −128.8 | p10= | −98.23 |
| p01= | 0.9513 | p01= | 0.7611 | p01= | 0.6958 | p01= | 0.7392 |
| p20= | 13.93 | p20= | 15.81 | p20= | 12.82 | p20= | 11.84 |
| p11= | 0.01817 | p11= | 0.001912 | p11= | −0.01452 | p11= | −0.02464 |
| p02= | −0.0001009 | p02= | −5.894e−05 | p02= | −4.279e−05 | p02= | −4.481e−05 |
| p21= | −0.00324 | p21= | −0.00316 | p21= | −0.002379 | p21= | −0.001773 |
| p12= | 1.946e−06 | p12= | 3.107e−06 | p12= | 3.565e−06 | p12= | 3.464e−06 |
| p03= | 2.744e−09 | p03= | 5.617e−10 | p03= | −1.006e−10 | p03= | 1.883e−10 |

FIG−7

$f(x) = p1*x^3 + p2*x^2 + p3*x + p4$
where x is normalized by mean 39 and std 5.164
f(x): [p00 p10 p01 p20 p11 p02 p21 p12 p03]

| P00 | p10 | p01 | p20 | p11 | p02 | p21 | p12 | p03 |
|---|---|---|---|---|---|---|---|---|
| p1= -0.5523 | p1= -24.75 | p1= -0.005809 | p1= 2.467 | p1= 0.002326 | p1= 2.74e-06 | p1= -0.0003141 | p1= 5.164e-08 | p1= -2.04e-10 |
| p2= -148.6 | p2= 12.49 | p2= 0.09733 | p2= -1.192 | p2= 0.002558 | p2= -1.833e-05 | p2= 0.0002192 | p2= -5.258e-07 | p2= 1.03e-09 |
| p3= -35.69 | p3= 68.39 | p3= -0.08343 | p3= -4.23 | p3= -0.02156 | p3= 2.044e-05 | p3= 0.001055 | p3= 5.835e-07 | p3= -8.244e-10 |
| p4= 135 | p4= -155.7 | p4= 0.7138 | p4= 14.49 | p4= -0.006688 | p4= -4.812e-05 | p4= -0.002802 | p4= 3.415e-06 | p4= 7.61e-11 |

TIRE CORNERING STIFFNESS ESTIMATION SYSTEM AND METHOD

FIELD OF THE INVENTION

The invention relates generally to tire monitoring systems for collecting measured tire parameter data during vehicle operation and, more particularly, to systems utilizing such tire sensor-based data in vehicle control systems.

BACKGROUND OF THE INVENTION

It is desirable to ascertain cornering stiffness of a vehicle tire in order to optimize control commands (active front/rear steering input, yaw control command) to achieve vehicle stability and safety without degrading driver intentions. Heretofore, a robust and high fidelity system and method for determining tire cornering stiffness in real time has not been achieved. Accordingly, there remains a need for a tire cornering stiffness determination system and method that is both robust and accurate and which can adapt to changes to tire conditions during operation of a vehicle.

SUMMARY OF THE INVENTION

In one aspect of the invention, a tire cornering stiffness estimation system and method is provided for a supportive tire to a vehicle, the tire having multiple tire-specific measurable parameters. The system employs a multiple tire-affixed sensors mounted to the tire for operably measuring the tire-specific parameters and generating tire-specific information. One or more accelerometer(s) are mounted to the hub supporting the tire to generate a hub accelerometer signal. A model-based tire cornering stiffness estimator is included to generate a model-derived tire cornering stiffness estimation based upon the hub accelerometer signal adapted by the tire-specific information.

In another aspect, the cornering stiffness estimation system and conducts a frequency domain spectral analysis of the hub accelerometer signal by the model-based tire cornering stiffness estimator.

According to a further aspect, the tire cornering stiffness estimator employs as estimator inputs: a load estimation for the object vehicle tire; temperature of the vehicle tire, air pressure within a cavity of the vehicle tire, a tire ID identifying the vehicle tire by tire type and a wear estimation on a tread of the vehicle tire.

The tire cornering stiffness estimation system and method, in another aspect, obtains the hub accelerometer signal from the vehicle CAN bus.

Definitions

"ANN" or "Artificial Neural Network" is an adaptive tool for non-linear statistical data modeling that changes its structure based on external or internal information that flows through a network during a learning phase. ANN neural networks are non-linear statistical data modeling tools used to model complex relationships between inputs and outputs or to find patterns in data.

"Aspect ratio" of the tire means the ratio of its section height (SH) to its section width (SW) multiplied by 100 percent for expression as a percentage.

"Asymmetric tread" means a tread that has a tread pattern not symmetrical about the center plane or equatorial plane EP of the tire.

"Axial" and "axially" means lines or directions that are parallel to the axis of rotation of the tire.

"Chafer" is a narrow strip of material placed around the outside of a tire bead to protect the cord plies from wearing and cutting against the rim and distribute the flexing above the rim.

"Circumferential" means lines or directions extending along the perimeter of the surface of the annular tread perpendicular to the axial direction.

"Dugoff Model" is an empirical tire model providing analytical relations for the longitudinal and lateral forces as functions of the slip angle and slip ratio. It accounts for the coupling between the side and longitudinal forces.

"Equatorial Centerplane (CP)" means the plane perpendicular to the tire's axis of rotation and passing through the center of the tread.

"Footprint" means the contact patch or area of contact created by the tire tread with a flat surface as the tire rotates or rolls.

"Groove" means an elongated void area in a tire wall that may extend circumferentially or laterally about the tire wall. The "groove width" is equal to its average width over its length. A grooves is sized to accommodate an air tube as described.

"Inboard side" means the side of the tire nearest the vehicle when the tire is mounted on a wheel and the wheel is mounted on the vehicle.

"Lateral" means an axial direction.

"Lateral edges" means a line tangent to the axially outermost tread contact patch or footprint as measured under normal load and tire inflation, the lines being parallel to the equatorial centerplane.

"Net contact area" means the total area of ground contacting tread elements between the lateral edges around the entire circumference of the tread divided by the gross area of the entire tread between the lateral edges.

"Non-directional tread" means a tread that has no preferred direction of forward travel and is not required to be positioned on a vehicle in a specific wheel position or positions to ensure that the tread pattern is aligned with the preferred direction of travel. Conversely, a directional tread pattern has a preferred direction of travel requiring specific wheel positioning.

"Outboard side" means the side of the tire farthest away from the vehicle when the tire is mounted on a wheel and the wheel is mounted on the vehicle.

"Peristaltic" means operating by means of wave-like contractions that propel contained matter, such as air, along tubular pathways.

"Piezoelectric Film Sensor" a device in the form of a film body that uses the piezoelectric effect actuated by a bending of the film body to measure pressure, acceleration, strain or force by converting them to an electrical charge.

"Radial" and "radially" means directions radially toward or away from the axis of rotation of the tire.

"Rib" means a circumferentially extending strip of rubber on the tread which is defined by at least one circumferential groove and either a second such groove or a lateral edge, the strip being laterally undivided by full-depth grooves.

"Sipe" means small slots molded into the tread elements of the tire that subdivide the tread surface and improve traction, sipes are generally narrow in width and close in the tires footprint as opposed to grooves that remain open in the tire's footprint.

"Tread element" or "traction element" means a rib or a block element defined by having a shape adjacent grooves.

"Tread Arc Width" means the arc length of the tread as measured between the lateral edges of the tread.

BRIEF DESCRIPTION OF THE DRAWINGS

The invention will be described by way of example and with reference to the accompanying drawings in which:

FIG. 7 is a table showing model coefficients for different four inflation levels.

DETAILED DESCRIPTION OF THE INVENTION

Figure 1:
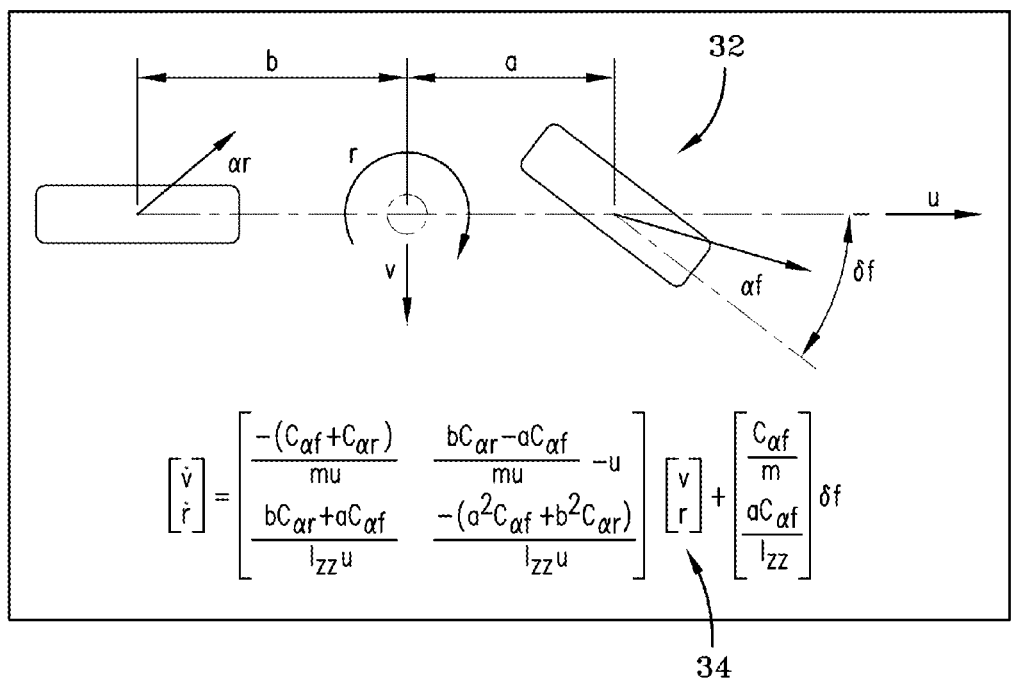
FIG. 1 is a two degree of freedom (DOF) bicycle vehicle model and state-space representation of the model describing lateral and yaw dynamics.
Figure 2A:
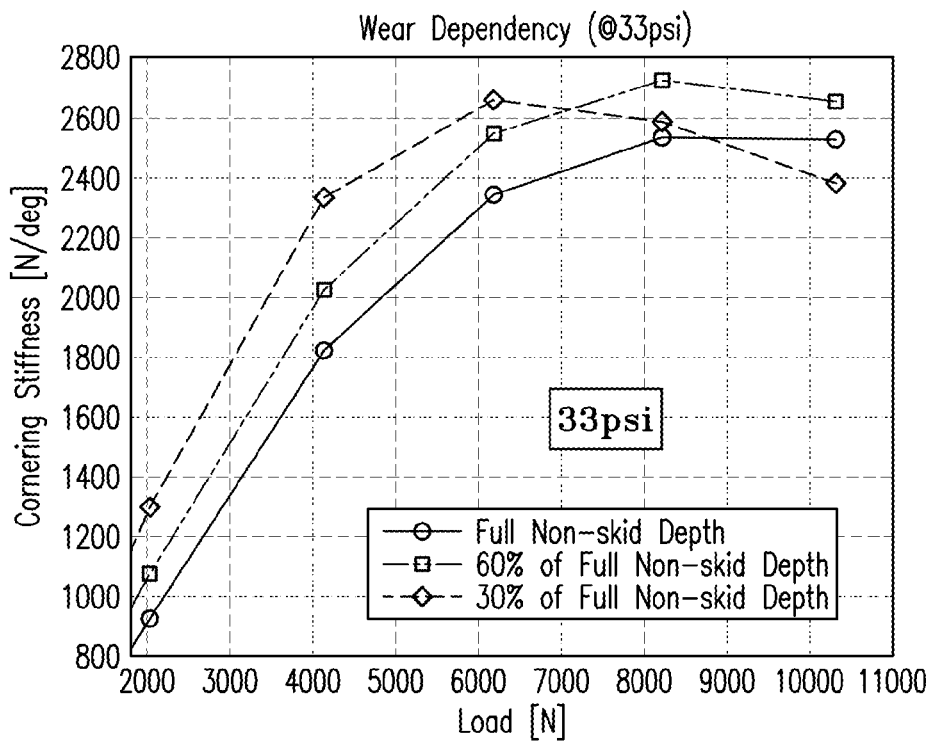
FIGS. 2A and 2B are graphs showing cornering stiffness dependency on tire load and tread wear for two respective inflation pressures.
Figure 2B:
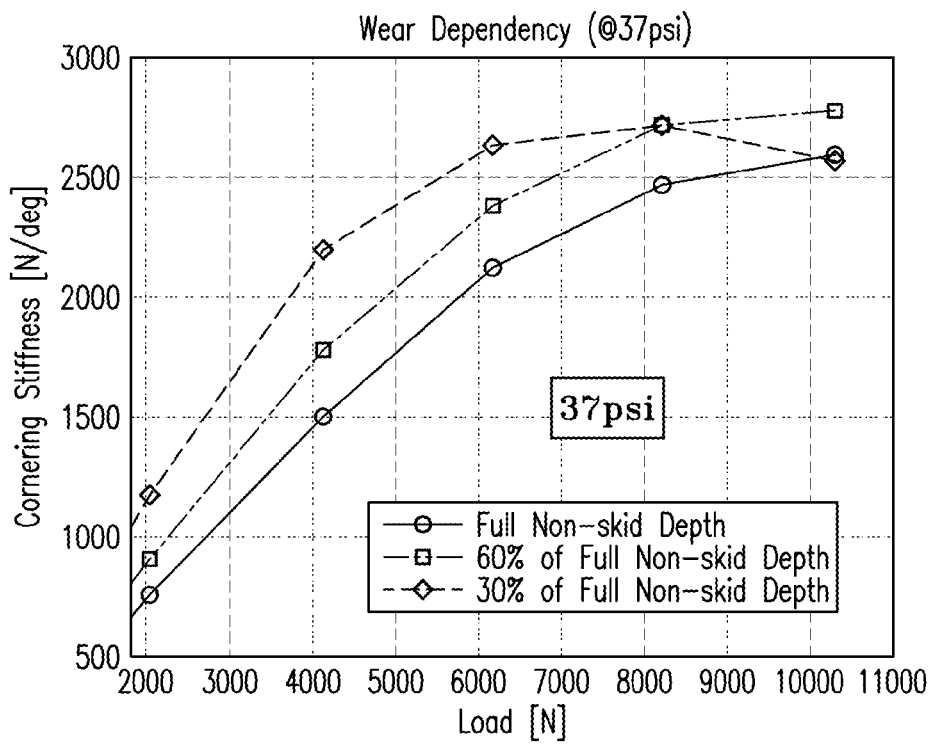
Figure 2C:
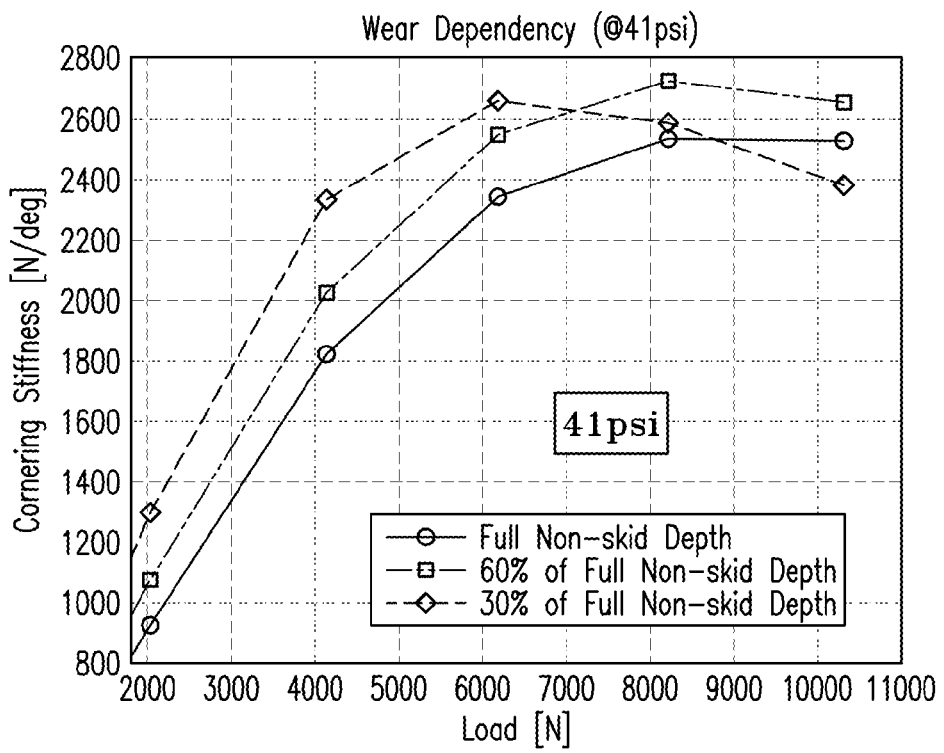
FIGS. 2C and 2D are additional graphs showing cornering stiffness dependency on tire load and tread wear for two additional inflation pressures.
Figure 2D:
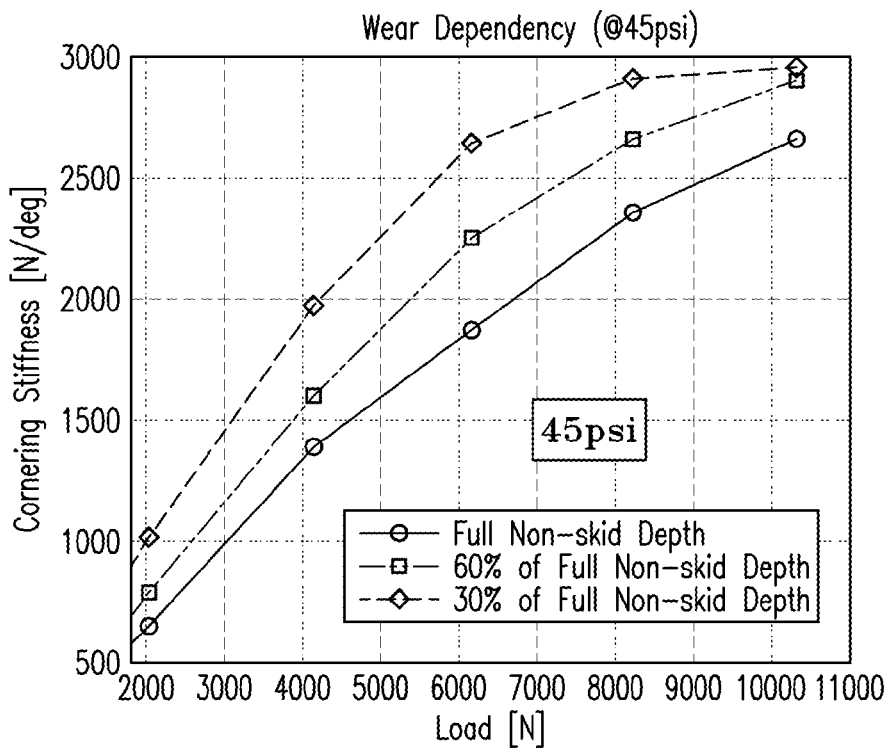

Referring to FIG. 1, a two degree of freedom (DOF) bicycle vehicle model and state-space expression for the model describing lateral and yaw dynamics is shown. The expression of FIG. 1 follows the definitional key where u is the vehicle forward speed, v the vehicle lateral speed, r the yaw rate, m the vehicle mass, $I_{zz}$ the yaw moment of inertia, $C_{af}$ and $C_{ar}$ are the front and rear cornering stiffness (per axle), $\delta_f$ the front wheel steering angle, and a and b are the distances from the vehicle center of gravity to front and rear axles, respectively.

By way of background, the subject invention is directed to a tire force model adaptation to tire-based information obtained from tire-attached sensors in order to make a tire cornering stiffness estimation. As seen in the FIG. 5, schematic representation of the subject cornering stiffness estimation system and method 10. The system includes a vehicle 12 supported by one or more tires 14. The purpose of the system 10 is to dynamically estimate cornering stiffness for each tire 14 supporting the vehicle 12. The tire 14 is of conventional build, having a tire tread 16, a pair of sidewalls 18 and an air containing cavity 22. A tire-attached sensor 20 is affixed to the inner liner defining cavity 22 as shown. The sensor 20, referred to herein as a tire pressure monitoring sensor is a package of sensors and transponders intended to measure tire temperature and cavity pressure. In addition, a tire identification transponder is present, programmed to provide a unique tire-specific identification. Such sensors and transponders are commercially available and may be attached to the tire 14 by suitable means such as adhesive.

The cornering stiffness estimation system 10 develops an estimate of the loading on the tire 14 by means of a load estimation method 23. The load estimation 23 is based upon a dynamic tire load estimator configured as presented in co-pending U.S. Patent Application Publication No. 2014/0278040, filed Mar. 12, 2013 and published Sep. 18, 2014, entitled VEHICLE DYNAMIC LOAD ESTIMATION SYSTEM AND METHOD hereby incorporated herein in its entirety. In addition, the system 10 uses as an adaptive input a wear estimation method 24 based upon vehicle-based sensors provided from the CAN bus 25 of the vehicle 12. The CAN bus 25 input of vehicle-based information into the wear estimation method 24 results in an estimation of tire wear state of the tire tread 16. A suitable wear estimation method, referred herein as an "indirect" wear state estimation method, is found in co-pending U.S. application Ser. No. 13/917,691, filed Jun. 14, 2013, entitled TIRE WEAR STATE ESTIMATION SYSTEM AND METHOD hereby incorporated by reference in its entirety herein. The "indirect" tire wear state estimation algorithm is used to generate tread depth estimation indirectly; that is, without the use of tire mounted tread depth measuring sensors. As such the difficulty of implementing and maintaining accurate tire-based sensor tread depth measurement is avoided. The indirect tire wear state estimation algorithm utilizes a hub acceleration signal which is accessible via the vehicle CAN bus 25 from vehicle based sensors. The hub acceleration signal is analyzed and an estimation is made as to tread depth or wear. The tread depth used may be the percentage tread wear left or a quantitative value of tread wear depth left on the tire.

The collective information provided by the tire-based sensors and transponders, referred to as tire-based information, constitute adaptation inputs 26 into a tire cornering stiffness adaptation model 28 that outputs the object cornering stiffness estimation 30. Operation of the model 28 and adaptation are based upon cornering stiffness dependency on the inputs 26 as will be explained below.

With reference to FIG. 1, vehicle control systems are based on tire characteristics (cornering stiffness, peak grip level). However these characteristics fluctuate under varying operating conditions of the tire (temperature change, pressure change, tire wear state change, load change) which affects the accuracy of the vehicle stability control. The availability of a high fidelity tire model with suitable adaptation terms would facilitate the online computation of the optimized control commands such as active front/rear steering input, yaw control to achieve vehicle stability and safety without degrading driver intentions. The subject method and system provides such an adaptation model for the cornering stiffness parameter by using inflation pressure, tire wear state, load, and tire temperature as adaptation inputs.

The subject system uses information from tire-attached sensors and transducers 20 and utilizes different tire-affixed sensor within a sensor fusion framework. A model 32 describing the motion of the vehicle is selected, such as that shown in FIG. 1, known as the "bicycle model" which includes tire cornering stiffness parameters. These parameters describe the tire-road contact and are unknown and time-varying. Hence, in order to fully make use of the single track or bicycle model, the parameters affecting corning stiffness are used. Following is a state-space representation 34 of the model:

$$\begin{bmatrix} \dot{v} \\ \dot{r} \end{bmatrix} = \begin{bmatrix} \frac{-(C_{af}+C_{ar})}{mu} & \frac{bC_{ar}-aC_{af}}{mu}-u \\ \frac{bC_{ar}-aC_{af}}{I_{zz}u} & \frac{-(a^2C_{af}+b^2C_{ar})}{I_{zz}u} \end{bmatrix} \begin{bmatrix} v \\ r \end{bmatrix} + \begin{bmatrix} \frac{C_{af}}{m} \\ \frac{aC_{af}}{I_{zz}} \end{bmatrix} \delta_f$$

The dependency of cornering stiffness in a tire to tire wear state and tire load is demonstrated graphically by test results in FIGS. 2A through 2D showing cornering stiffness vs. load for 33, 37, 41, and 45 psi inflation pressure. Full 60 percent and 30 percent of tread depth were used in the tests and their respective effect on cornering stiffness were examined under the four inflation pressures selected. A 35 percent change in the tire cornering stiffness was measured for the three different tread depths evaluated. It will further be noted by a comparison of the four graphs to each other that cornering stiffness changes both with changes in the tire inflation pressure and changes in load as evidenced by the plots.

Figure 3:
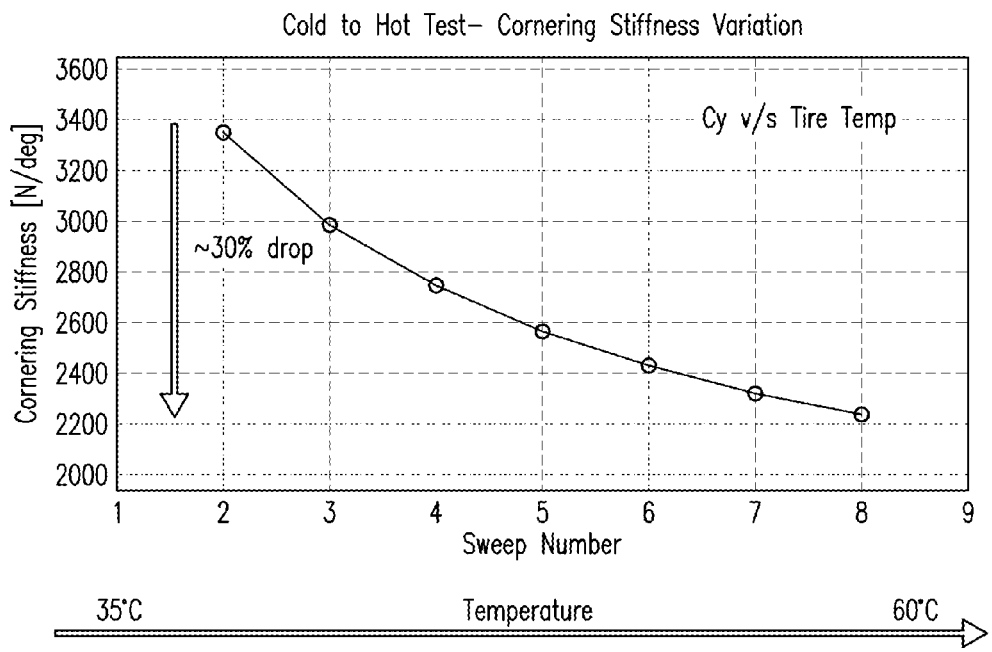
FIG. 3 is a graph showing cornering stiffness dependency on tire temperature.

In FIG. 3, the dependency of cornering stiffness to tire temperature is seen. A sweep was conducted varying temperature between 35° C. and 60° C. The effect of the change in temperature on the measured cornering stiffness Cy is shown. A 30 percent drop in cornering stiffness was measured between 35° C. and 60° C.

Figure 4:
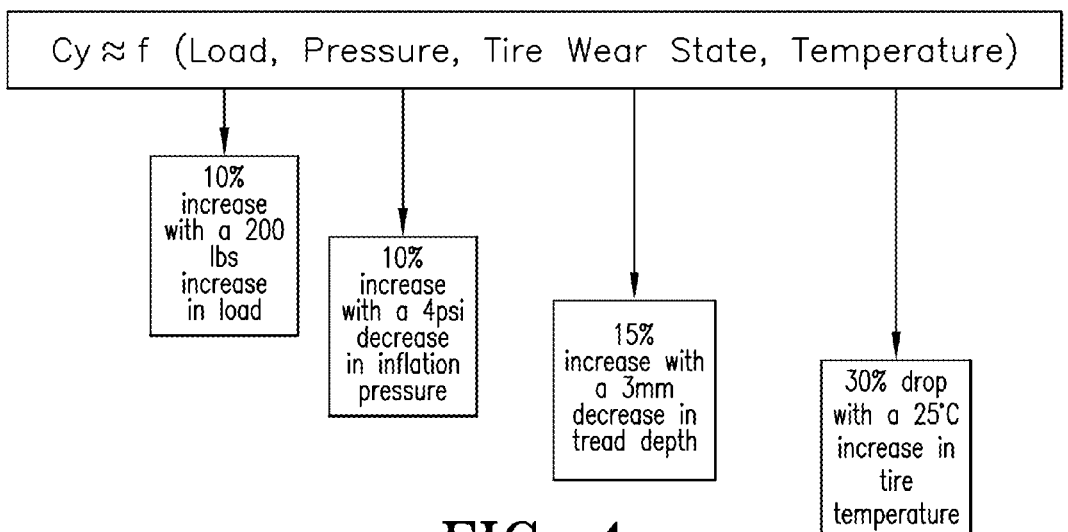
FIG. 4 is a chart summary of cornering stiffness sensitivities to load, pressure, tire wear state and temperature.

The test results and sensitivities are summarized in FIG. 4. As seen, cornering stiffness is a function of load, pressure, tire wear state and temperature and such dependencies are important in a cornering stiffness estimation system and method. Regarding load, a 10 percent increase in cornering stiffness from a 200 pound increase in load is noted. For inflation pressure, a 10 percent increase in cornering stiffness for a 4 psi decrease in inflation pressure. A 15 percent increase in cornering stiffness occurs with a 3 mm decrease in tread depth and a 30 percent drop with a 25° C. increase in tire temperature.

The subject model capturing the dependencies between the tire cornering stiffness, tire wear state and tire load is shown below. A Polynomial model (third order in load and second order in tread depth) results in a good fit as shown in FIGS. 6A through 6D. The tests were conducted at inflation pressures of 33, 37, 41 and 45 psi. Goodness of fit resultant correlation coefficient R was 0.998 at 33 psi, 0.998 at 37 psi, 0.999 at 41 psi and 0.999 at 45 psi.

Model Fit:

fit result$(x,y)$=$p00+p10*x+p01*y+p20*x^2+p11*x*y+p02*y^2+p21*x^2*y+p12*x*y^2+p03*y^3$ Coeff=[p00 p10 p01 p20 p11 p02 p21 p12 p03];
Coeff_33=[−23.23 −179.5 0.9513 13.93 0.01817 −0.0001009 −0.00324 1.946e-06 2.744e-09];
Coeff_37=[126.6 −178.9 0.7611 15.81 0.001912 −5.894e-05 −0.00316 3.107e-06 5.617e-10];
Coeff_41=[98.89 −128.8 0.6958 12.82 −0.01452 −4.279e-05 −0.002379 3.565e-06 −1.006e-10];
Coeff_45=[−107.9 −98.23 0.7392 11.84 −0.02464 −4.481e-05 −0.001773 3.464e-06 1.883e-10];

The model thus is seen to give a good fit for all pressure conditions.

The expression used in the model for cornering stiffness Cy is as follows:

Cy=$(p20+p21*load)*tread depth^2+(p10+p11*load+p12*load^2)*tread depth+(p00+p01*load+p02*load^2+p03*load^3)$ The table shown in FIG. 7 summarizes the model coefficients for each of the four pressure levels evaluated. The model coefficients verify the dependency of cornering stiffness estimation to tire pressure.

Model fitting through the adaptation of coefficients to inflation pressure changes is further demonstrated by the coefficient-against-pressure graphs of FIGS. 8, 9, 10, 11, 12, 13, 14, 15, and 16. Model fit is expressed as follows:

Cy=$(p20+p21*load)*tread depth^2+(p10+p11*load+p12*load^2)*tread depth+(p00+p01*load+p02*load^2+p03*load^3)$ where x is normalized by mean 39 and standard deviation 5.164.

As seen, coefficients defined are: p1, p2, p3, and p4.

Figures 16, 17:
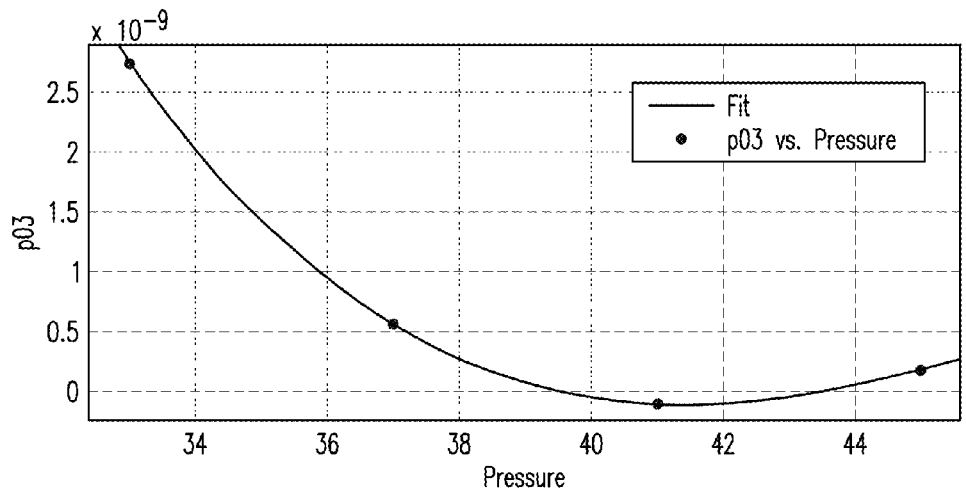
FIG. 16 is a model fitting graph for a coefficient p03 vs. pressure.
FIG. 17 is a table showing model fitting coefficients determinations.
Figure 18A:
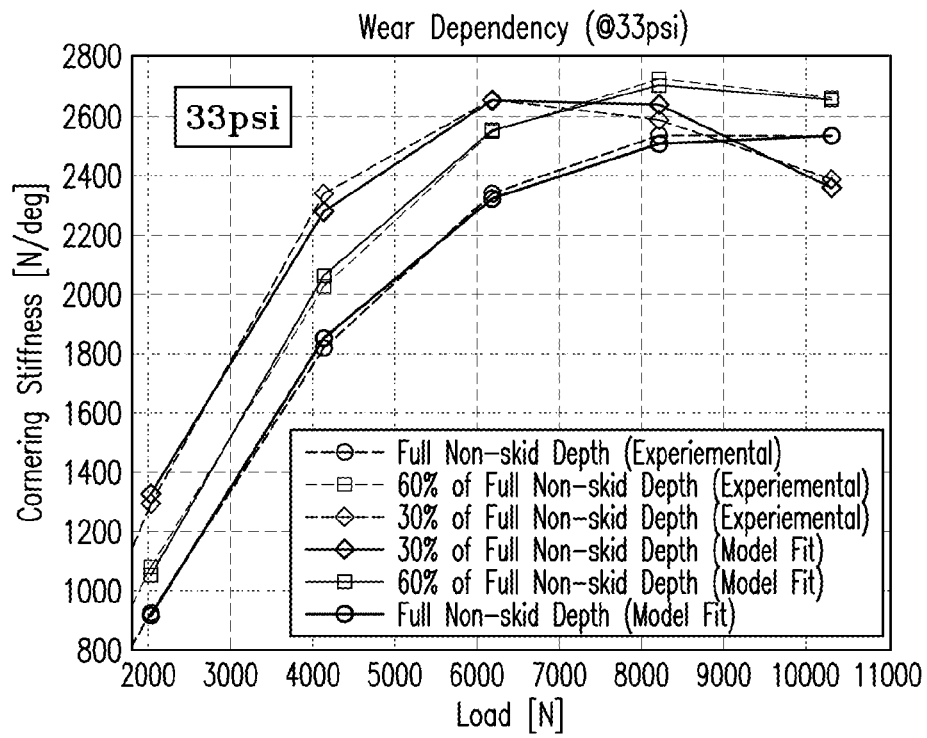
FIGS. 18A through 18D are graphs showing cornering stiffness dependency on tire wear state and load at four different tire inflation levels.
Figure 18B:
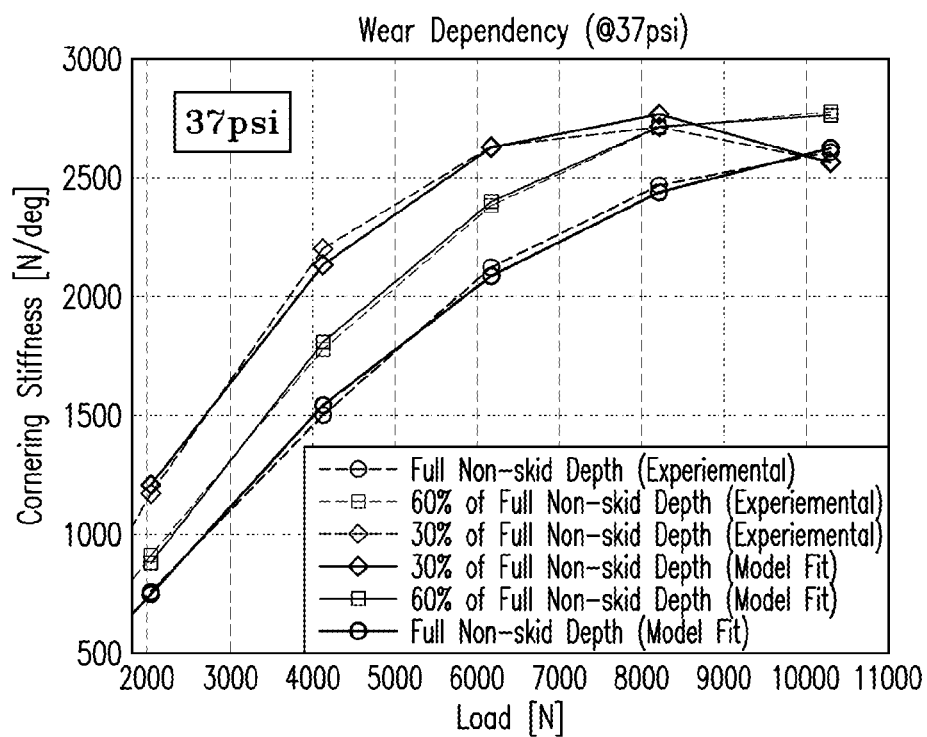
Figure 18C:
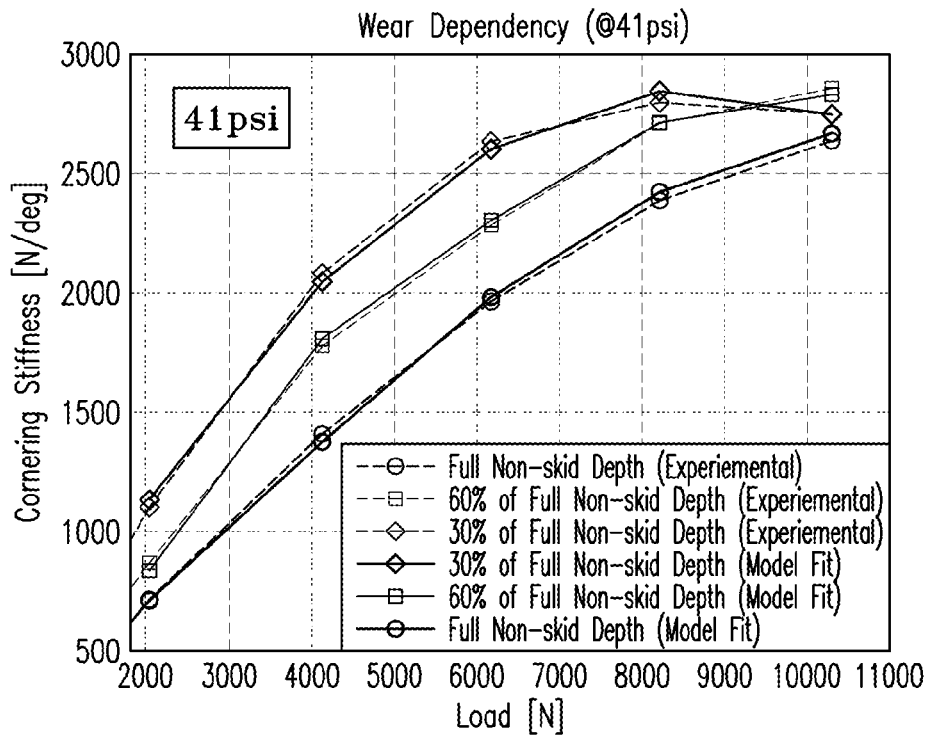
Figure 18D:
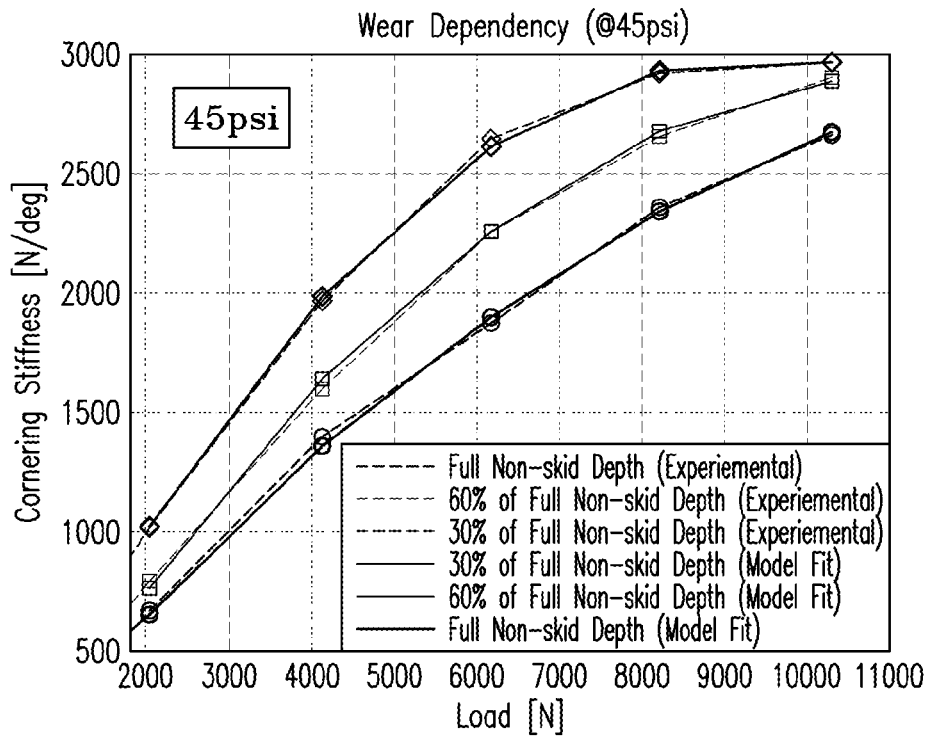

FIG. 17 shows in tabular form the coefficients for an estimation of cornering stiffness subject to the following expression:

$$Cy=(p20+p21*load)*tread\ depth^2+(p10+p11*load+p12*load^2)*tread\ depth+(p00+p01*load+p02*load^2+p03*load^3)$$

where the coefficients [p00, p10, p01, p20, p11, p02, p21, p12, p03] are pressure dependent and given by the following expression:

$$[p00\ p10\ p01\ p20\ p11\ p02\ p21\ p12\ p03]=p1*x^3+p2*x^2+p3*x+p4$$

Here x is normalized by mean 39 and standard deviation 5.164.

Model fitting results with pressure adapted coefficients are shown graphically in FIGS. 18A through 18D for the four pressure settings: 33, 37, 41, and 45 psi. Tread wear at full non-skid, 60 percent, 30 percent are plotted for both experimental and Model fit. The plotting of Cy vs. load is shown comparing experimental to Model fit and indicate the model is effective in predicting cornering stiffness Cy at different load, pressure, and tread wear.

Figure 19A:
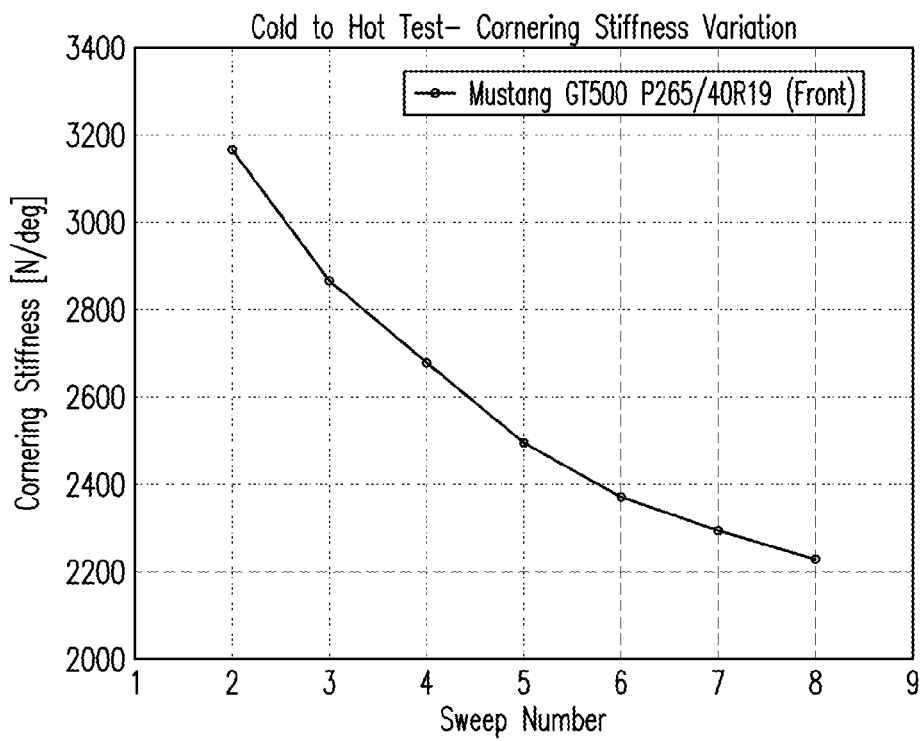
FIGS. 19A through 19C are test result graphs of cornering stiffness, peak grip level, and mean temperature in a cold to hot test temperature variation test.
Figure 19B:
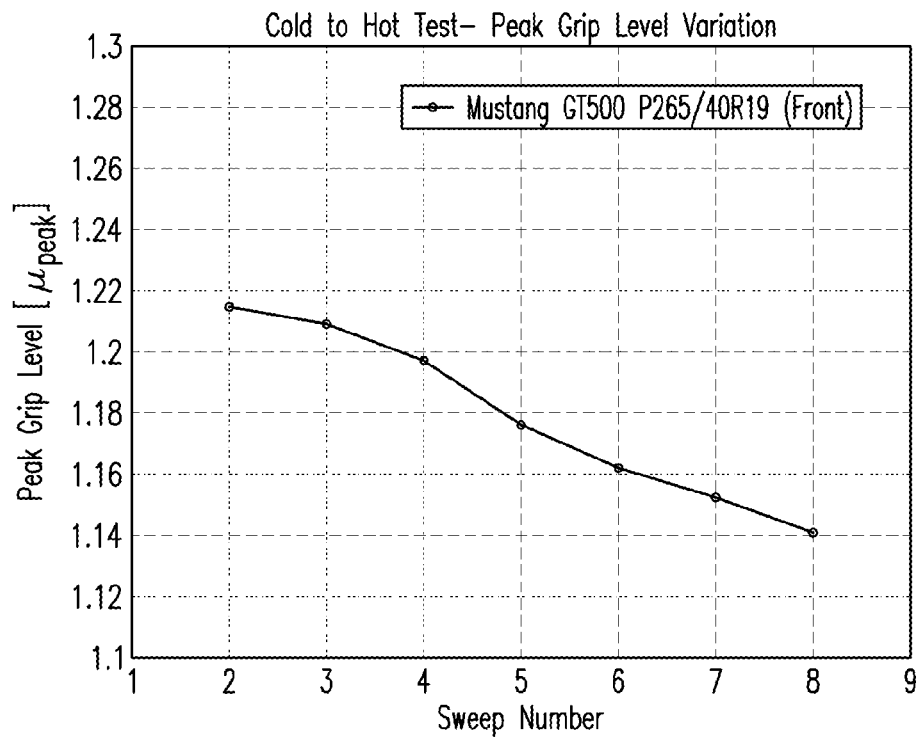
Figure 19C:
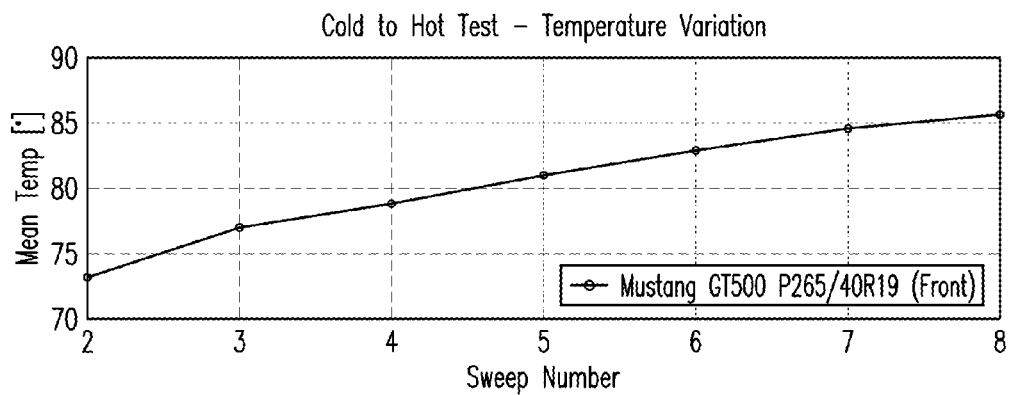
Figure 20:
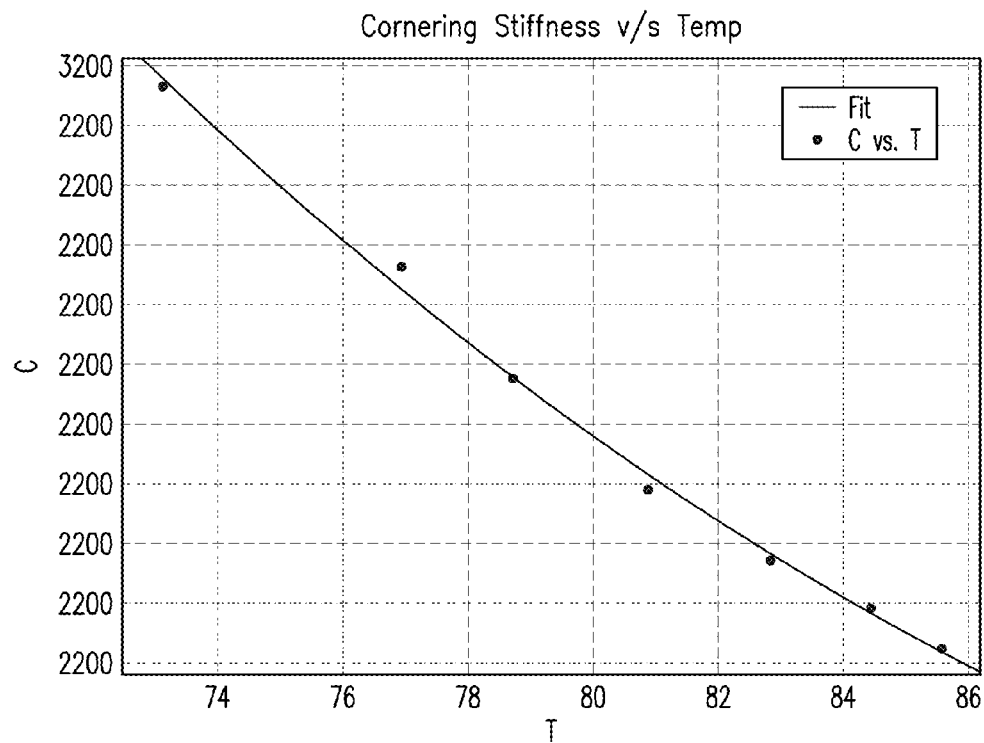
FIG. 20 is a graph showing cornering stiffness-temperature variation model fit.

In FIG. 19A, a cold to hot test results are shown graphically for a tested Mustang GT500 vehicle fitted with Goodyear P265/40R19 front tires. The cornering stiffness in the cold to hot test is shown. In FIG. 19B, peak grip level variation for the cold to hot test is graphed. In FIG. 19C, temperature variation for the test is shown graphically. FIG. 20 shows the graph of cornering stiffness during the test as temperature is varied.

The dependence of cornering stiffness on the tire temperature can be captured by introducing a polynomial scaling factor as follows.
Model Fit:

$$f(x)=p1*x^2+p2*x+p3$$

Coefficients (with 95 percent confidence bounds):
p1=1.761 (0.04273, 3.48)
p2=−356.5 (−629.8, −83.09)
p3=1.983e+04 (8978, 3.067e+04)

Cornering stiffness adaptation model thus becomes as follows:

$$Cy=(p20+p21*load)*tread\ depth^2+(p10+p11*load+p12*load^2)*tread\ depth+(p00+p01*load+p02*load^2+p03*load^3)*Temperature\ Scaling\ Factor$$

Figure 5:
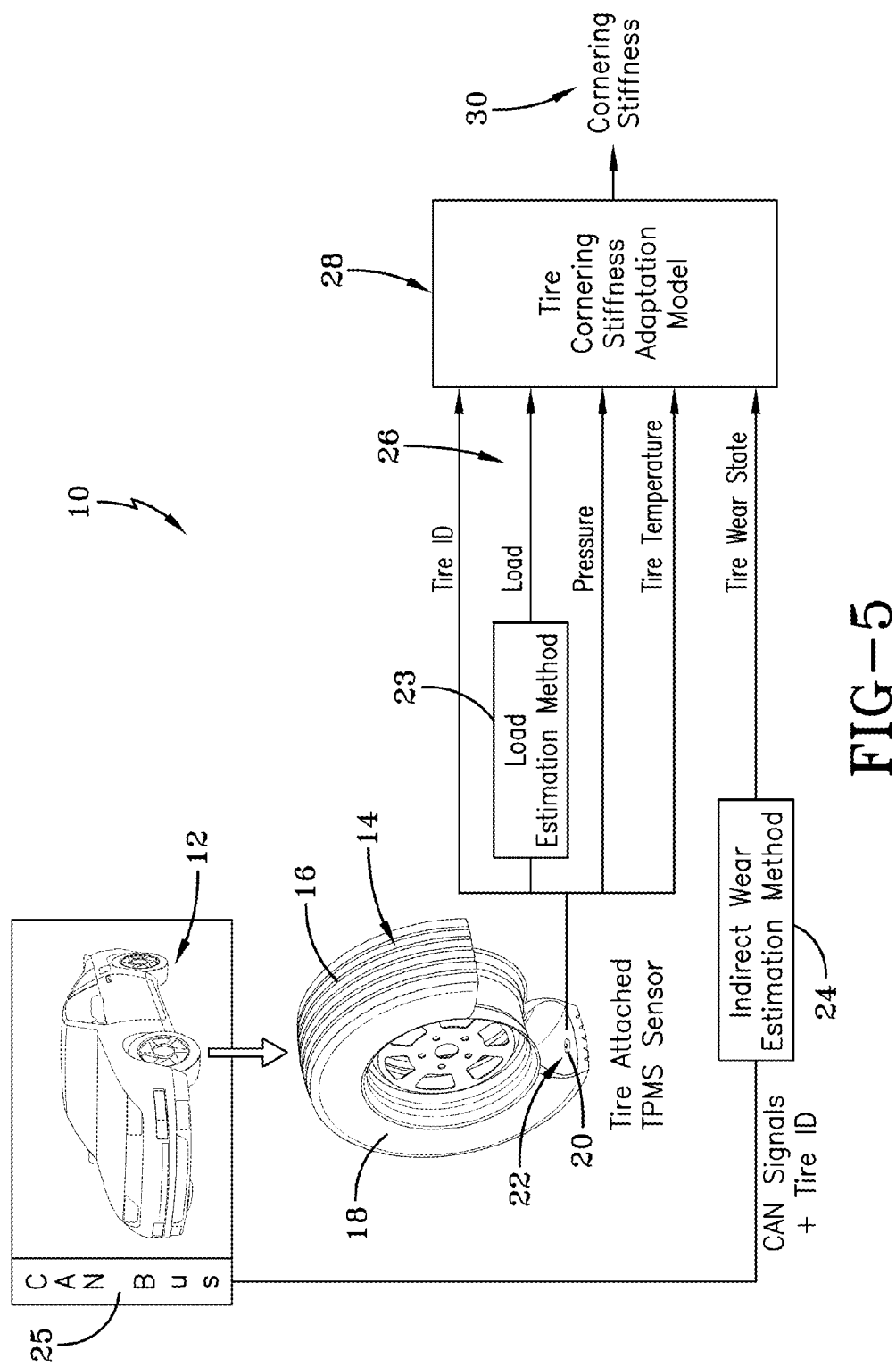
FIG. 5 is an adaptation model for determining a cornering stiffness estimation.
Figure 6A:
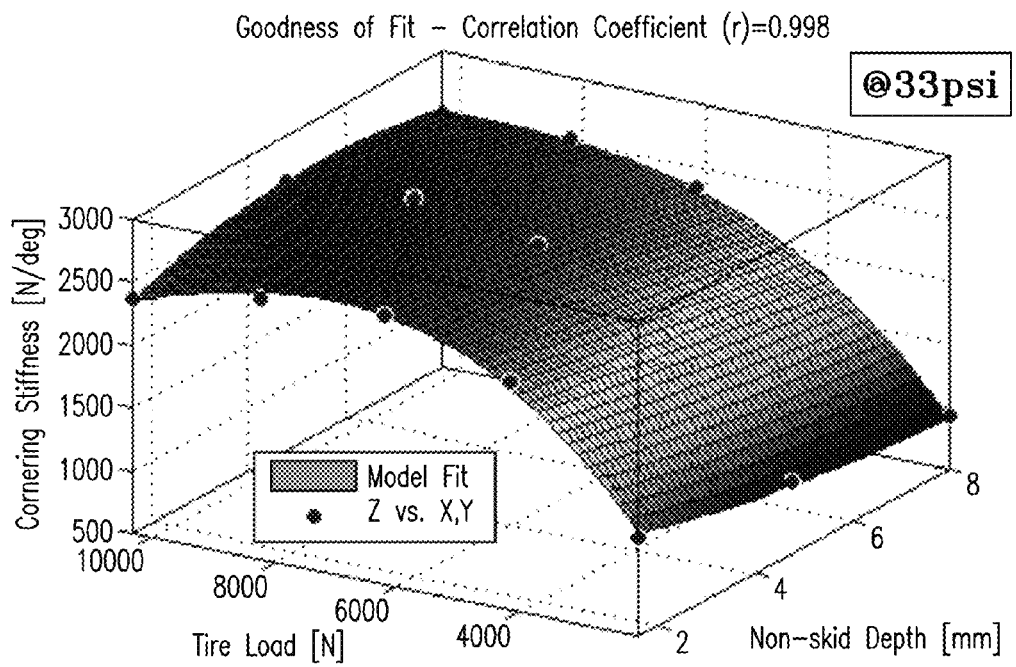
FIG. 6A through 6D are graphs showing goodness of fit of the model in estimating cornering stiffness at four inflation pressures.
Figure 6B:
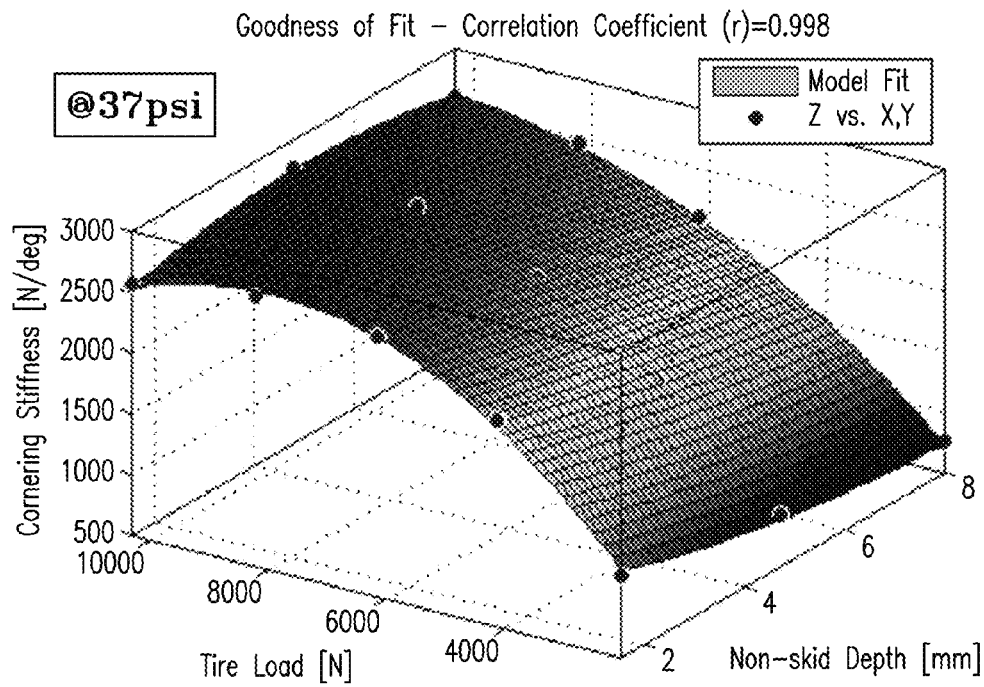
Figure 6C:
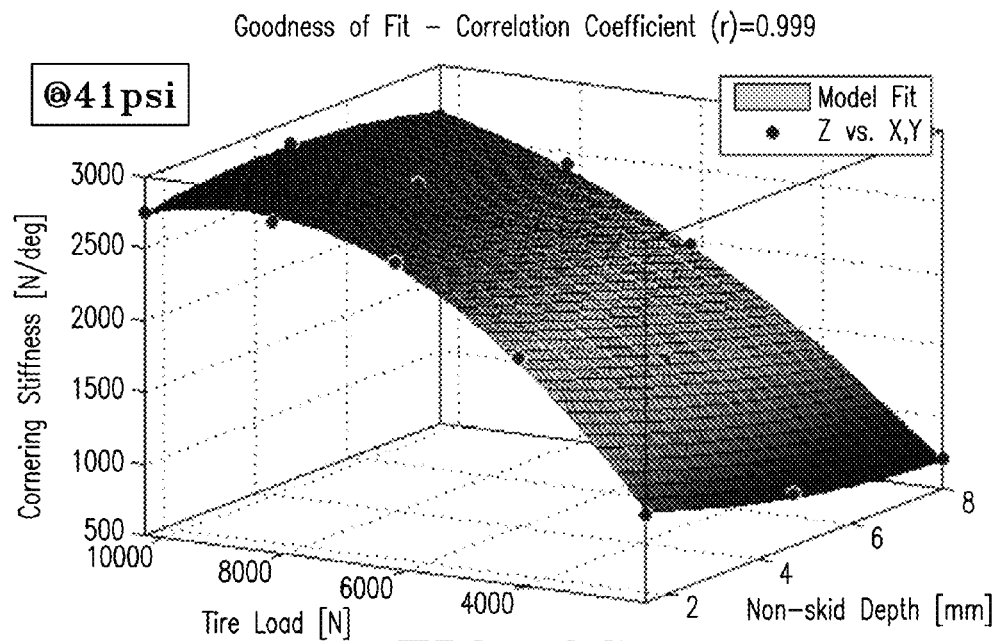
Figure 6D:
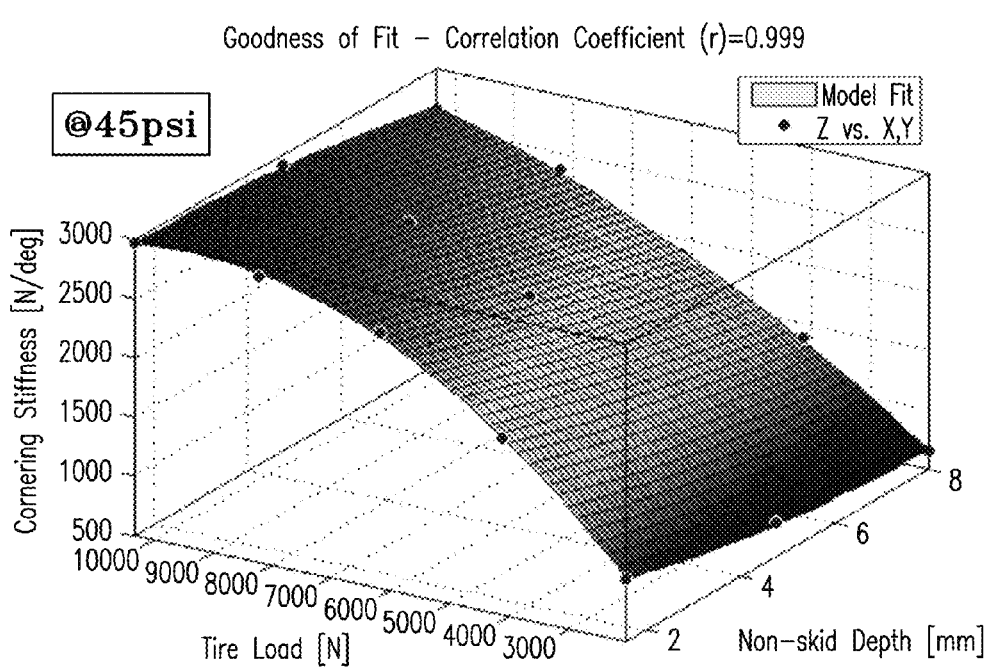
Figure 8:
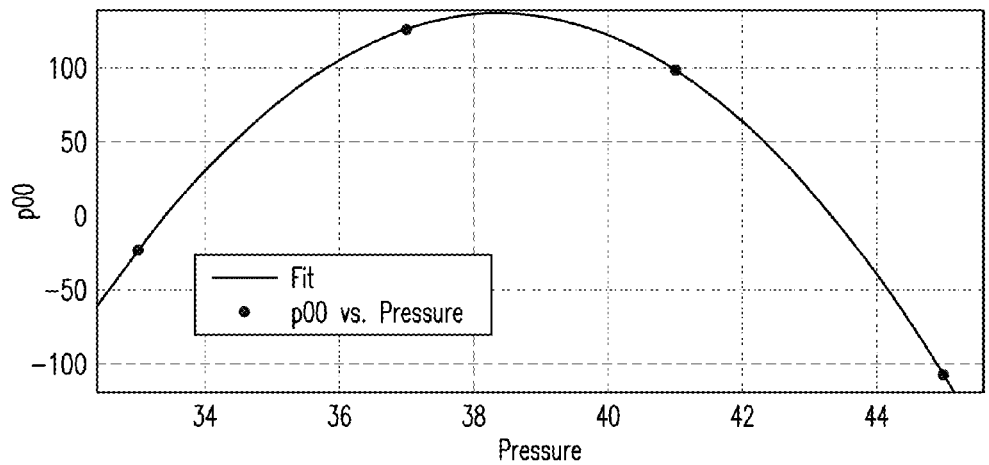
FIG. 8 is a graph showing model fitting, adapting model coefficients to inflation pressure changes for a coefficient p00 vs. pressure.
Figure 9:
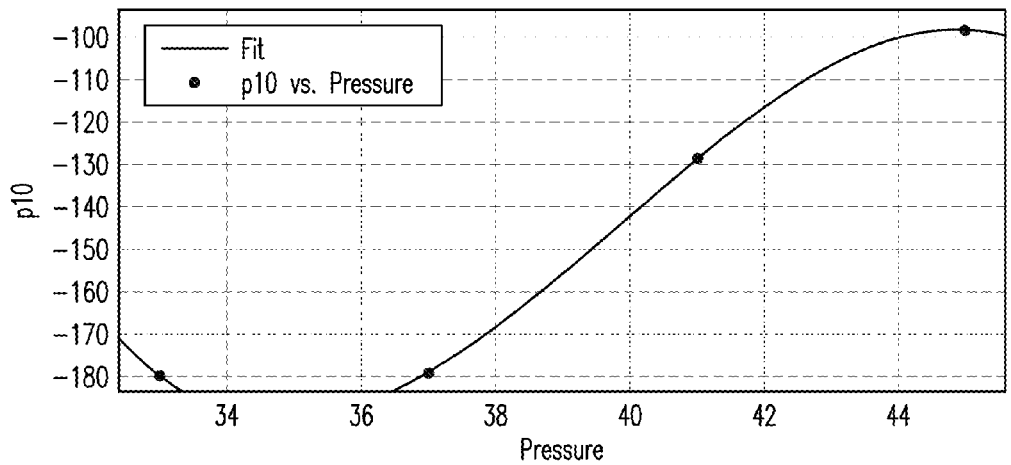
FIG. 9 is a model fitting graph for a coefficient p10 vs. pressure.
Figure 10:
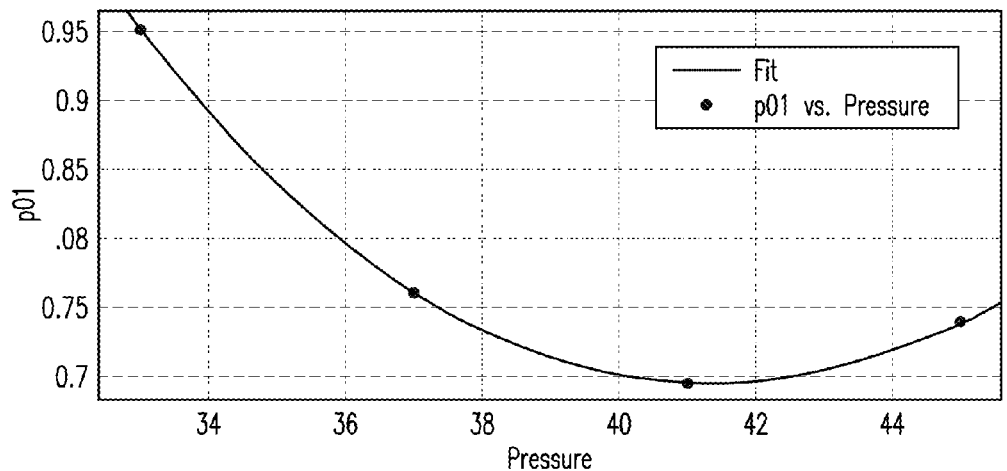
FIG. 10 is a model fitting graph for a coefficient p01 vs. pressure.
Figure 11:
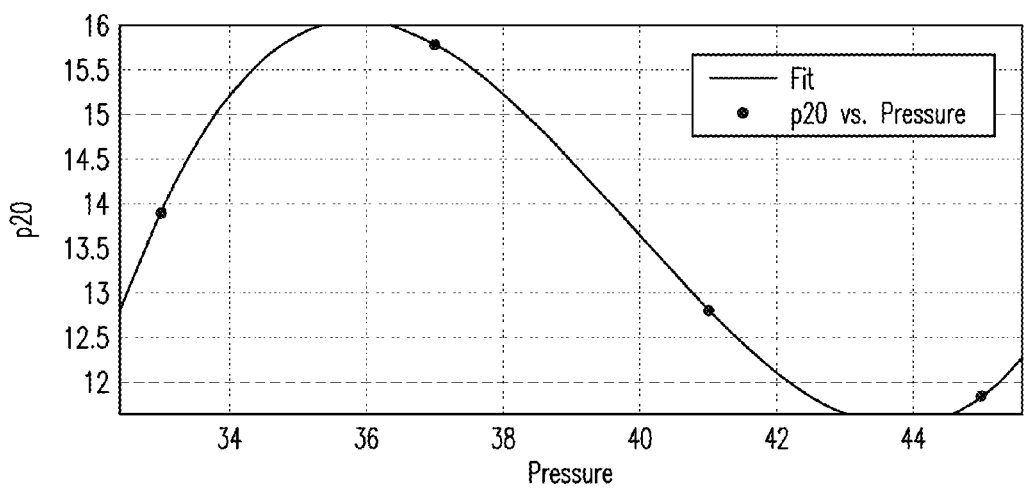
FIG. 11 is a model fitting graph for a coefficient p20 vs. pressure.
Figure 12:
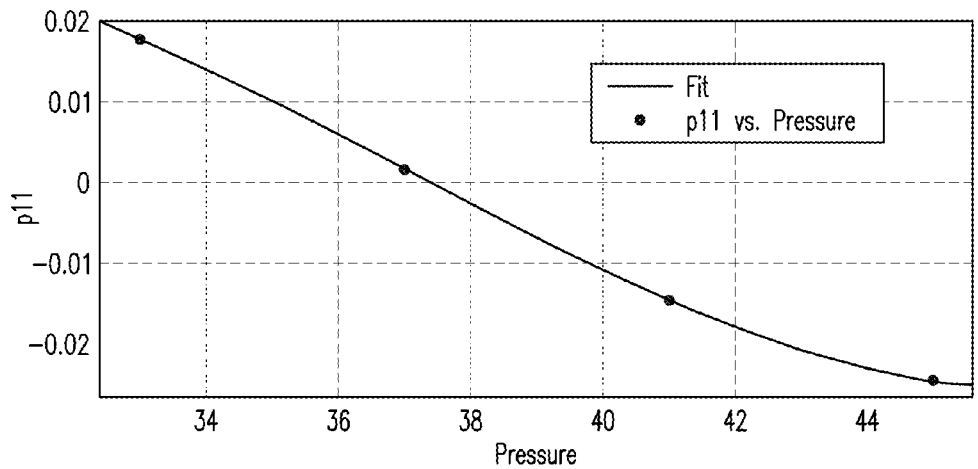
FIG. 12 is a model fitting graph for a coefficient p11 vs. pressure.
Figure 13:
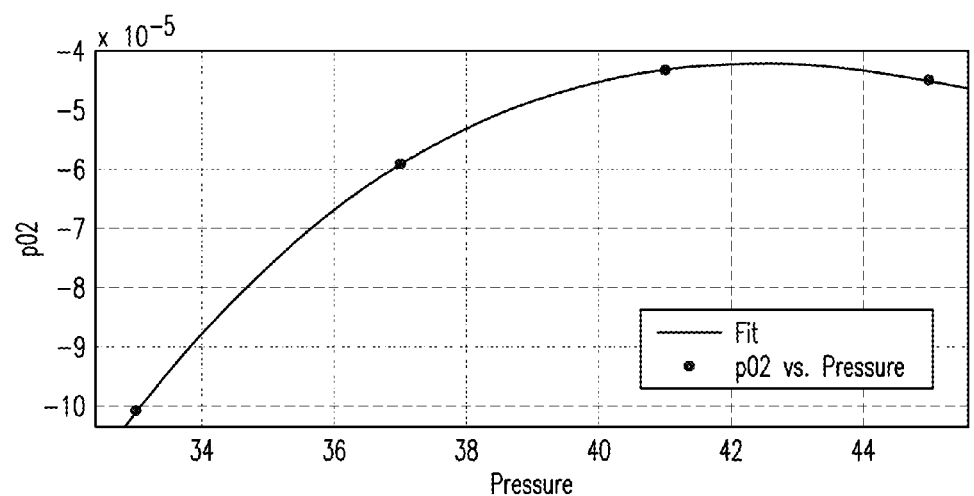
FIG. 13 is a model fitting graph for a coefficient p02 vs. pressure.
Figure 14:
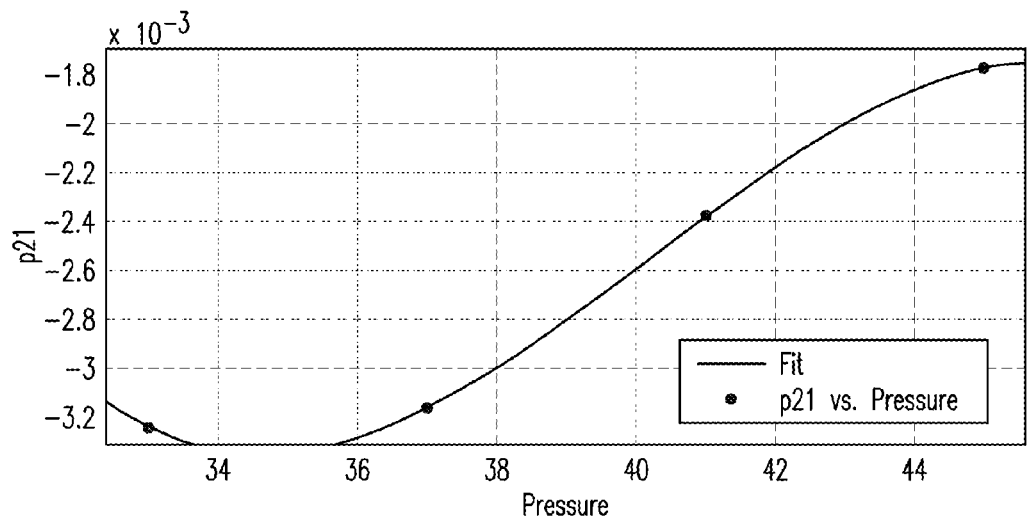
FIG. 14 is a model fitting graph for a coefficient p21 vs. pressure.
Figure 15:
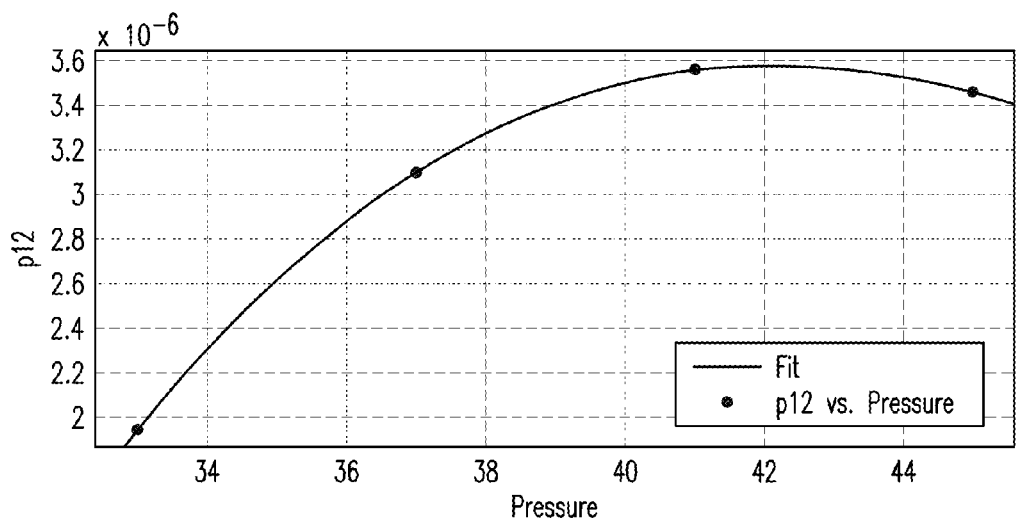
FIG. 15 is a model fitting graph for a coefficient p12 vs. pressure.

From the foregoing and in reference to FIG. 5, the subject tire cornering stiffness estimation system and method 10 is provided for analyzing and estimating cornering stiffness for each supportive tire 14 to a vehicle 12. The tire has multiple tire-specific measurable parameters of tire inflation pressure, tire ID (required for using tire-specific model coefficients), tire load, tire wear state and tire temperature. The tire ID is recognized by a reading of a tire-mounted transducer and the coefficients for that particular tire are then used by the model in making its estimation.

The system employs a multiple tire-affixed sensors 20 mounted to the tire for operably measuring the tire-specific parameters and generating tire-specific information. The tire inflation pressure, load, temperature and tire ID information is available from a tire attached TPMS sensor 20 equipped with tire ID information. One or more accelerometer(s) are mounted to the hub supporting the tire to generate a hub accelerometer signal. The model-based tire cornering stiffness estimator generates a model-derived tire cornering stiffness estimation based upon the hub accelerometer signal (used to estimate loading) and adapted by the tire-specific information (tire ID, pressure, temperature, and wear state).

Tire wear state is derived by doing a frequency domain/spectral analysis of the suspension hub-mounted accelerometer signal as taught in co-pending U.S. application Ser. No. 13/917,691, filed Jun. 14, 2013.

The tire cornering stiffness estimator for Cy employs as estimator inputs 26: a load estimation for the object vehicle tire, temperature of the vehicle tire, air pressure within a cavity of the vehicle tire and the tire ID used to generate model coefficients by recognition of tire-type, and a wear estimation on a tread of the vehicle tire. The hub accelerometer signal is obtained from the vehicle CAN-bus.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A tire cornering stiffness estimation system comprising:
a vehicle supported by at least one vehicle tire mounted to a hub, the vehicle tire having a tire cavity and a ground-engaging tread, and the tire having a plurality of tire-specific measureable parameters, the tire-specific measureable parameters including a load estimation for the one vehicle tire, a temperature of the one vehicle tire, an air pressure within a cavity of the one vehicle tire, and a tire identification identifying the one vehicle tire;
a plurality of tire-affixed sensors mounted to the tire operably measuring the tire-specific measureable parameters to generate tire-specific information;
at least one accelerometer mounted to the hub and generating a hub accelerometer signal to provide a wear estimation for the ground-engaging tread of the one vehicle tire;
a tire cornering stiffness estimator employing a model operable to generate a tire cornering stiffness estimation based upon the hub accelerometer signal and adapted by the tire-specific information.

2. The cornering stiffness estimation system of claim 1, wherein the tire cornering stiffness estimator operably conducts a frequency domain spectral analysis of the hub accelerometer signal.

3. The cornering system estimation of claim 1, wherein the hub accelerometer signal is provided to the tire cornering stiffness estimator from a vehicle CAN-bus.

4. A tire cornering stiffness estimation system comprising:
a vehicle supported by at least one vehicle tire mounted to a hub, the vehicle tire having a tire cavity and a ground-engaging tread, and the tire having a plurality of tire-specific measureable parameters, the tire-specific measureable parameters including a load estimation for the one vehicle tire, a temperature of the one vehicle tire, an air pressure within a cavity of the one vehicle tire, and a tire identification identifying the one vehicle tire;
a plurality of tire-affixed sensors mounted to the tire operably measuring the tire-specific measureable parameters to generate tire-specific information;
at least one accelerometer mounted to the hub and generating a vehicle CAN-bus hub accelerometer signal to provide a wear estimation for the ground-engaging tread of the one vehicle tire;
a tire cornering stiffness estimator employing a model operable to generate a tire cornering stiffness estimation based upon the vehicle CAN-bus hub accelerometer signal and adapted by the tire-specific information.

5. The cornering stiffness estimation system of claim 4, wherein the tire cornering stiffness estimator operably conducts a frequency domain spectral analysis of the vehicle CAN-bus hub accelerometer signal.

6. A method of estimating tire cornering stiffness comprising:
equipping a vehicle with at least one vehicle tire mounted to a hub, the vehicle tire having a tire cavity and a ground-engaging tread, and the tire having a plurality of tire-specific measureable parameters, the tire-specific measureable parameters including a load estimation for the one vehicle tire, a temperature of the one vehicle tire, an air pressure within a cavity of the one vehicle tire, and a tire identification identifying the one vehicle tire;
affixing a plurality of tire-based sensors to the tire to operably measure the tire-specific measureable parameters and thereby generate tire-specific information;
mounting at least one accelerometer to the hub to operably generate a hub accelerometer signal to provide a wear estimation for the ground-engaging tread of the one vehicle tire;
generating from a tire cornering stiffness estimator employing a model a tire cornering stiffness estimation based upon the hub accelerometer signal and adapted by the tire-specific information.

7. The method of claim 6, further comprising conducting a frequency domain spectral analysis of the hub accelerometer signal by the tire cornering stiffness estimator.

8. The method of claim 7, wherein further comprising obtaining the hub accelerometer signal from a vehicle CAN-bus.

* * * * *